United States Patent
Morita et al.

(10) Patent No.: US 6,531,542 B1
(45) Date of Patent: Mar. 11, 2003

(54) SPHERICAL CROSSLINKED ORGANIC PARTICLES SUSPENSIONS AND METHODS OF PREPARING SPHERICAL CROSSLINKED ORGANIC PARTICLES AND SUSPENSIONS

(75) Inventors: Yoshitsugu Morita, Chiba Prefecture (JP); Kazuo Kobayashi, Chiba Prefecture (JP); Ryuji Tachibana, Chiba Prefecture (JP)

(73) Assignee: Dow Corning Toray Silicone Company, Ltd., Tokyo (JP)

( * ) Notice: Subject to any disclaimer, the term of this patent is extended or adjusted under 35 U.S.C. 154(b) by 121 days.

(21) Appl. No.: 09/626,135

(22) Filed: Jul. 26, 2000

(51) Int. Cl.$^7$ ............................................... C08L 83/04
(52) U.S. Cl. ................... 524/837; 524/862; 525/100; 525/106; 525/478; 525/479; 523/340
(58) Field of Search ................. 525/106, 100, 525/478, 479; 523/223, 340; 524/837, 862

(56) References Cited

U.S. PATENT DOCUMENTS

| | | | | |
|---|---|---|---|---|
| 4,761,454 A | * | 8/1988 | Oba et al. ................. | 525/478 |
| 4,962,165 A | | 10/1990 | Bortnick et al. ........... | 525/479 |
| 4,987,169 A | * | 1/1991 | Kuwata et al. | |
| 5,891,966 A | * | 4/1999 | Murry et al. .............. | 525/100 |
| 5,908,951 A | * | 6/1999 | Kobayashi et al. ......... | 556/479 |
| 5,928,660 A | * | 7/1999 | Kobayashi et al. ......... | 424/401 |
| 5,969,035 A | * | 10/1999 | Meinhardt et al. .......... | 524/731 |
| 5,969,039 A | * | 10/1999 | Kobayashi et al. ......... | 524/837 |

FOREIGN PATENT DOCUMENTS

| | | | |
|---|---|---|---|
| CA | 2236056 | * | 10/1998 |
| JP | 04-117456 | | 4/1992 |

* cited by examiner

Primary Examiner—Daniel S. Metzmaier
(74) Attorney, Agent, or Firm—Jim L. De Cesare; Catherine U. Brown

(57) ABSTRACT

Spherical crosslinked organic particles exhibit a good dispersibility in thermoplastic resins, thermosetting resins, paints, coatings, cosmetics, rubbers, and toners and carriers employed in electrostatic development. Highly efficient methods for preparing these crosslinked organic particles are provided. Suspensions of crosslinked organic particles have excellent handling properties, and are highly blendable with other components. Highly efficient methods for preparing these suspensions are also provided. The spherical crosslinked organic particles have an average particle size of 0.1–500 $\mu$m, and can be prepared by emulsifying in water using an emulsifying agent, a fluid composition containing (A) an organic compound that has at least 2 aliphatically unsaturated bonds in each molecule, (B) a silicon-containing organic compound that has at least 2 silicon-bonded hydrogen atoms in each molecule, (C) an hydrosilylation reaction catalyst, crosslinking the fluid composition by carrying out an hydrosilylation reaction, and thereafter removing water.

4 Claims, No Drawings

SPHERICAL CROSSLINKED ORGANIC PARTICLES SUSPENSIONS AND METHODS OF PREPARING SPHERICAL CROSSLINKED ORGANIC PARTICLES AND SUSPENSIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

FIELD OF THE INVENTION

This invention is directed to crosslinked organic particles and suspensions thereof, and to methods for preparing the crosslinked organic particles and their suspensions. More particularly, this invention relates to spherical crosslinked organic particles that are highly dispersible in thermoplastic resins, thermosetting resins, paints, coatings, cosmetics, rubbers, and toners and carriers employed in electrostatic development. The invention additionally relates to very efficient methods for preparing crosslinked organic particles. Crosslinked organic particle suspensions have excellent handling properties and are highly blendable with other components. The invention also relates to very efficient methods for preparing such suspensions.

BACKGROUND OF THE INVENTION

Non-thermally-softenable, solvent-insoluble crosslinked organic particles have an excellent resistance to heat, cold, and weathering, and excellent electrical properties, and are used as blocking inhibitors, cracking inhibitors, flatting agents, tactile sensation improvers, and lubricants for thermoplastic resins, thermosetting resins, paints, coatings, films, cosmetics, rubbers, and toners and carriers employed in electrostatic development. These crosslinked organic particles can be produced by (i) grinding or crushing a crosslinked organic material which produces irregularly shaped crosslinked organic particles; by (ii) producing solvent-insoluble crosslinked organic particles by dispersing a vinyl monomer and a compound bearing a plurality of unsaturated groups in a medium, and then inducing crosslinking by polymerization; and (iii) by dispersing epoxy resin in a medium and then crosslinking it using a curing agent to produce crosslinked organic particles.

However, such crosslinked organic particles suffer from poor dispersibility when blended into thermoplastic resins, thermosetting resins, paints, coatings, cosmetics, rubbers, and toners and carriers employed in electrostatic development.

BRIEF SUMMARY OF THE INVENTION

It is therefore an object of the invention to provide spherical crosslinked organic particles that are highly dispersible in thermoplastic resins, thermosetting resins, paints, coatings, cosmetics, rubbers, and toners and carriers employed in electrostatic development. Another object is to provide highly efficient methods for preparing crosslinked organic particles. An additional object is to provide crosslinked organic particle suspensions that have excellent handling properties and are highly blendable with other components. Yet another object is to provide highly efficient methods for preparing such suspensions.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

Crosslinked organic particles according to the invention are spherical. They have an average particle size of 0.1 to 500 μm and are afforded by an hydrosilylation-induced crosslinking of a fluid composition comprising:

(A) an organic compound that contains at least 2 aliphatically unsaturated bonds in each molecule,
(B) a silicon-containing organic compound that has at least 2 silicon-bonded hydrogen atoms in each molecule, and
(C) a catalyst for the hydrosilylation reaction.

Crosslinked organic particle suspensions of the invention contain water, an emulsifying agent, the crosslinked organic particles, and the particles are dispersed in the water.

One method for preparing the crosslinked organic particles is by emulsifying a fluid composition comprising:

(A) an organic compound that contains at least 2 aliphatically unsaturated bonds in each molecule,
(B) a silicon-containing organic compound that has at least 2 silicon-bonded hydrogen atoms in each molecule, and
(C) a catalyst for the hydrosilylation reaction, in water using an emulsifying agent, crosslinking the fluid composition by carrying out hydrosilylation, and thereafter removing the water.

Another method for preparing crosslinked organic particles comprises emulsifying a fluid composition of components (A) and (B) in water using an emulsifying agent, thereafter adding component (C), then crosslinking the composition by carrying out hydrosilylation, and finally removing the water.

One method for preparing crosslinked organic particle suspensions according to the invention is by emulsifying a fluid composition comprising:

(A) an organic compound that contains at least 2 aliphatically unsaturated bonds in each molecule,
(B) a silicon-containing organic compound that has at least 2 silicon-bonded hydrogen atoms in each molecule, and
(C) a catalyst for the hydrosilylation reaction, in water using an emulsifying agent, and crosslinking the fluid composition by carying out hydrosilylation.

Another method for preparing crosslinked organic particle suspensions of the invention is by emulsifying a fluid composition of components (A) and (B) in water using an emulsifying agent, thereafter adding component (C), and then crosslinking the composition by carrying out hydrosilylation.

Crosslinked organic particles according to the invention are spherically-shaped crosslinked organic particles, and they are provided by an hydrosilylation-induced crosslinking of a fluid composition comprising components (A) through (C) described above. These particles should have an average particle size in the range from 0.1 to 500 μm, and preferably have an average particle size in the range from 0.1 to 200 μm. It is quite difficult to prepare crosslinked organic particles with an average particle size below the lower limit of the given range. Crosslinked organic particles with an average particle size exceeding the upper limit of the given range exhibit an increasingly impaired dispersibility when blended into organic resins, paints, coatings, and cosmetics.

Organic compound (A) contains at least 2 aliphatically unsaturated bonds in each molecule. The aliphatically unsaturated group in (A) can be a group present in a molecular chain terminal position, or it can be present in a pendant position on the molecular chain. It can be alkenyl such as vinyl, allyl, butenyl, and pentenyl; alkynyl such as ethynyl; or a cyclic unsaturated group such as the norbornene group or dicyclopentadienyl. The aliphatically unsaturated group can also be a group within the molecular chain, in which case it can be an enylene group like vinylene or propenylene. Groups present in a terminal or pendant position on the molecular chain such as vinyl and allyl are preferred for the aliphatically unsaturated group in (A). The state of (A) is not critical, and component (A) can be a solid or a liquid, with a liquid being preferred. When component (A) is a solid, it will be necessary to preliminarily dissolve it in component (B) when such dissolution is possible, or component (A) would have to be dissolved in an organic solvent. While the molecular weight of component (A) is not critical, its average molecular weight is preferably in the range from 50 to 50,000.

Component (A) can be exemplified by dienes such as pentadiene, hexadiene, heptadiene, octadiene, nonadiene, cyclopentadiene, and cyclooctadiene; aromatic dienes such as divinylbenzene; ethers such as diallyl ether, triethylene glycol divinyl ether, cyclohexane dimethanol divinyl ether, and 1,2-divinyl glycol; diene esters such as diallyl isophthalate, diallyl phthalate, diallyl terephthalate, diallyl maleate, and triallyl trimellitate; oligomers from polymerization of any of the preceding; olefin oligomers that contain at least 2 aliphatically unsaturated bond-containing groups in each molecule, produced by polymerization of an olefin such as ethylene, propylene, butene, isobutene, pentene, or hexene; oligomers from polymerization of an alkenyl-functional acrylic monomer such as allyl (meth)acrylate, butenyl (meth)acrylate, methylbutenyl(meth)acrylate, methylpropenyl(meth)acrylate, heptenyl (meth)acrylate, and hexenyl (meth)acrylate; oligomers from copolymerization of acrylic monomer as listed above with a monomer such as methyl(meth)acrylate, ethyl(meth)acrylate, butyl(meth) acrylate, ethylhexyl(meth)acrylate, lauryl(meth)acrylate, styrene, α-methylstyrene, maleic acid, vinyl acetate, or allyl acetate; oligomers from reaction of an alkenyl isocyanate such as allyl isocyanate, (meth)acryloyl isocyanate, and 2-isocyanatoethyl (meth)acrylate) or an alkenyl-functional carboxylic acid anhydride such as itaconic anhydride, maleic anhydride, or tetrahydrophthalic anhydride, with an oligomer produced by copolymerization of such a monomer as referenced above and a hydroxyl-functional acrylic monomer such as 2-hydroxyethyl (meth)acrylate, 2-hydroxypropyl (meth)acrylate, or 4-hydroxybutyl (meth) acrylate; oligomers from reaction of an alkenyl alcohol such as allyl alcohol, butenol, 2-(allyloxy) ethanol, glycerol diallyl ether, cyclohexene methanol, methylbutenol, and oleyl alcohol with an oligomer produced by polymerization of isocyanate-functional acrylic monomers such as (meth) acryloyl isocyanate and 2-isocyanatoethyl (meth)acrylate), or with an oligomer produced by copolymerization of such an isocyanate-functional acrylic monomer with a monomer as referenced above; oligomers from reaction of an alkenyl-functional epoxy compound such as glycidyl (meth)acrylate and allyl glycidyl ether with an oligomer from polymerization of a carboxyl-functional monomer such as (meth)acrylic acid, itaconic acid, and maleic acid or with an oligomer from copolymerization of such carboxyl-functional monomers with a monomer as referenced above; polyethers from the ring-opening polymerization of allyl glycidyl ether using ethylene glycol as an initiator; polyethers from the ring-opening polymerization of vinylcyclohexane-1,2-epoxide using butanol, allyl alcohol, or propargyl alcohol as an initiator; alkenyl-functional polyesters from reaction of an alkenyl alcohol as referenced above, a polyhydric alcohol such as ethylene glycol, propylene glycol, 1,6-hexanediol, diethylene glycol, neopentyl glycol, the neopentyl glycol ester of hydroxypivalic acid, and trimethylolpropane, and a polybasic acid such as phthalic anhydride, isophthalic acid, terephthalic acid, adipic acid, azelaic acid, and trimellitic acid. Component (A) is preferably a diene, diene oligomer, or polyether.

Silicon-containing organic compound (B) contains at least two silicon-bonded hydrogen atoms in each molecule. Component (B) preferably has a viscosity at 25° C. in the range from 1 to 100,000 mPa·s, and particularly preferably in the range from 1 to 10,000 mPa·s. Silicon-containing organic compound (B) can be exemplified by organohydrogenpolysiloxanes, and organic polymers that contain diorganohydrogensilyl groups, with organohydrogenpolysiloxanes being preferred.

Organohydrogenpolysiloxanes encompassed by component (B) can have a straight-chain, branched-chain, cyclic, network, or partially branched straight-chain molecular structure, and can be exemplified by trimethylsiloxy-endblocked methylhydrogenpolysiloxanes; trimethylsiloxy-endblocked dimethylsiloxane-methylhydrogensiloxane copolymers; trimethylsiloxy-endblocked dimethylsiloxane-methylhydrogensiloxane-methylphenylsiloxane copolymers; dimethylhydrogensiloxy-endblocked dimethylpolysiloxanes; dimethylhydrogensiloxy-endblocked dimethylsiloxane-methylphenylsiloxane copolymers; dimethylhydrogensiloxy-endblocked methylphenylpolysiloxanes; organopolysiloxane copolymers containing $R_3SiO_{1/2}$, $R_2HSiO_{1/2}$, and $SiO_{4/2}$ siloxane units; organopolysiloxane copolymers containing $R_2HSiO_{1/2}$ and $SiO_{4/2}$ siloxane units; organopolysiloxane copolymers containing $RHSiO_{2/2}$ siloxane units and $RSiO_{3/2}$ or $HSiO_{3/2}$ siloxane units; and mixtures of two or more of such organopolysiloxanes.

The R group in these formulas represents non-alkenyl monovalent hydrocarbyl groups and can be an alkyl group such as methyl, ethyl, propyl, butyl, pentyl, hexyl, and heptyl; aryl such as phenyl, tolyl, xylyl, and naphthyl; aralkyl such as benzyl and phenethyl; and halogenated alkyl groups such as chloromethyl, 3-chloropropyl, and 3,3,3-trifluoropropyl.

Diorganohydrogensilyl-functional organic polymers encompassed by component (B) can be exemplified by oligomers from copolymerization of dimethylhydrogensilyl-functional acrylic monomers such as dimethylhydrogensilyl (meth)acrylate and dimethylhydrogensilylpropyl (meth) acrylate with monomers such as methyl (meth)acrylate, ethyl (meth)acrylate, butyl (meth)acrylate, ethylhexyl (meth)acrylate, lauryl (meth)acrylate, styrene, α-methylstyrene, maleic acid, vinyl acetate, and allyl acetate.

The content of component (B) in the composition provides preferably from 0.5 to 500 weight parts (B), and particularly preferably from 1 to 100 weight parts (B), in each case, for each 100 weight parts of component (A). The possibility of inadequate crosslinking arises when the component (B) content in the composition falls below the given lower limit of the range. A composition in which the component (B) content exceeds the upper limit of the range risks the evolution of hydrogen gas due to excess silicon-bonded hydrogen.

Component (C) is a catalyst for the hydrosilylation reaction. It should be a catalyst that promotes the hydrosilylation reaction in the composition, and thereby induce the crosslinking thereof. Component (C) is exemplified by platinum catalysts, rhodium catalysts, and palladium catalysts, with platinum catalysts being preferred. Platinum catalysts can be exemplified by Pt-on-finely divided silica, Pt-on-finely divided carbon, chloroplatinic acid, alcohol solutions of chloroplatinic acid, olefin complexes of platinum, alkenylsiloxane complexes of platinum, and carbonyl complexes of platinum.

The content of component (C) in the composition is not critical, but component (C) should be added in a catalytic quantity sufficient to promote the hydrosilylation reaction in the composition. When a platinum catalyst is used as component (C), it is preferably added in a quantity that will provide from $1 \times 10^{-7}$ to $1 \times 10^{-3}$ weight parts of platinum metal for each 100 weight parts of the total of components (A) and (B). Adequate crosslinking may not occur when the component (C) content in the composition is below the lower limit of the range. The use of quantities in excess of the upper limit of the range is not particularly effective, and such quantities are not economical.

Optional components that may be added to the composition are exemplified by inhibitors for controlling the hydrosilylation reaction; reinforcing fillers such as precipitated silica, fumed silica, calcined silica, and fumed titanium oxide; semi-reinforcing fillers such as crushed quartz, diatomaceous earth, aluminosilicates, iron oxide, zinc oxide, and calcium carbonate; any of the preceding fillers after surface treatment with an organosilicon compound such as hexamethyldisilazane, trimethylchlorosilane, polydimethylsiloxane, or polymethylhydrogensiloxane.

Noncrosslinking oils can also be admixed into the composition. Noncrosslinking oils can be exemplified by noncrosslinking silicone oils such as trimethylsiloxy-endblocked dimethylpolysiloxanes, trimethylsiloxy-endblocked methylphenylpolysiloxanes, trimethylsiloxy-endblocked dimethylsiloxane-methylphenylsiloxane copolymers, trimethylsiloxy-endblocked dimethylsiloxane-methyl(3,3,3-trifluoropropyl) siloxane copolymers, cyclic dimethylsiloxanes, and cyclic methylphenylsiloxanes. Other noncrosslinking organic oils which can be used are alkanes such as hexane and heptane, aromatic hydrocarbons such as benzene and toluene, chlorinated hydrocarbons such as carbon tetrachloride and methylene chloride, ketones such as methyl isobutyl ketone, alcohols such as undecyl alcohol, ethers such as dibutyl ether, esters such as isopropyl laurate and isopropyl palmitate, liquid paraffin, isoparaffin, hexyl laurate, isopropyl myristate, myristyl myristate, cetyl myristate, 2-octyldecyl myristate, isopropyl palmitate, 2-ethylhexyl palmitate, butyl stearate, decyl oleate, 2-octyldodecyl oleate, myristyl lactate, cetyl lactate, lanolin acetate, stearyl alcohol, cetostearyl alcohol, oleyl alcohol, avocado oil, almond oil, olive oil, cacao oil, jojoba oil, sesame oil, safflower oil, soy oil, camellia oil, squalane, persic oil, castor oil, mink oil, cottonseed oil, coconut oil, egg yolk oil, lard, glycol ester oils such as polypropylene glycol monooleate and neopentyl glycol 2-ethylhexanoate, polyhydric alcohol ester oils such as isostearate triglyceride and cocofatty acid triglycerides, and polyoxyalkylene ether oils such as polyoxyethylene lauryl ether and polyoxypropylene cetyl ether. The noncrosslinking oil preferably has a viscosity at 25° C. in the range from 1 to 100,000,000 mpa·s, and particularly preferably in the range from 2 to 10,000,000 mPa·s. The noncrosslinking oil is preferably present in the composition in an amount that provides from 0.1 to 5,000 weight parts of the noncrosslinking oil for each 100 weight parts of the composition, excluding the noncrosslinking oil.

Suspensions according to the invention contain the crosslinked organic particles as described above, an emulsifying agent, and water, and the particles are dispersed in the water. The crosslinked organic particles described above are used as the crosslinked organic particles in these suspensions. The emulsifying agent functions to improve the stability of the crosslinked organic particles in water. The emulsifying agent can be a cationic surfactant, an anionic surfactant, an amphoteric surfactant, a nonionic surfactant, or a mixture of surfactants.

Cationic surfactants can be exemplified by the salts of primary, secondary, and tertiary amines, alkyltrimethyl ammonium salts, dialkyldimethyl ammonium salts, tetraalkyl ammonium salts, trialkylbenzyl ammonium salts, alkylpyridinium salts, N,N-dialkylmorpholinium salts, and the salts of polyethylene polyamine aliphatic amides.

Anionic surfactants can be exemplified by the salts of aliphatic acids, the salts of alkylbenzene sulfonic acids, the salts of alkylnaphthalene sulfonic acids, the salts of alkylsulfonic acids, the salts of α-olefin sulfonic acids, the salts of dialkyl sulfosuccinates, α-sulfonated aliphatic acid salts, N-acyl-N-methyltaurates, alkyl sulfate salts, sulfated oils, polyoxyethylene alkyl ether sulfate salts, polyoxyethylene alkylphenyl ether sulfates, polyoxyethylene styrenated phenyl ether sulfates, alkyl phosphates, polyoxyethylene alkyl ether phosphates, polyoxyethylene alkylphenyl ether phosphates, and formaldehyde condensates of naphthalene sulfonates.

Amphoteric surfactants can be exemplified by N,N-dimethyl-N-alkyl-N-carboxymethyl ammonium betaines, N,N-dialkylamino alkylene carboxylates, N,N,N-trialkyl-N-sulfoalkylene ammonium betaines, N,N-dialkyl-N,N-bispolyoxyethylene ammonium sulfate ester betaines, and 2-alkyl-1-carboxymethyl-1-hydroxyethyl imidazolinium betaines.

Nonionic surfactants can be exemplified by polyoxyethylene alkyl ethers, polyoxyethylene alkenyl ethers, polyoxyethylene alkylphenyl ethers, polyoxyethylene polystyryl phenyl ethers, polyoxyethylene-polyoxypropylene glycols, and polyoxyethylene-polyoxypropylene alkyl ethers; aliphatic acid partial esters of polyhydric alcohols such as aliphatic acid esters of sorbitan, aliphatic acid esters of glycerol, aliphatic acid esters of decaglycerol, aliphatic acid esters of polyglycerol, aliphatic acid esters of ethylene glycol/pentaerythritol, and aliphatic acid esters of propylene glycol/pentaerythritol; polyoxyethylene adducts of aliphatic acid partial esters of polyhydric alcohols such as polyoxyethylene adducts of aliphatic acid esters of sorbitan, and polyoxyethylene adducts of aliphatic acid esters of glycerol; polyoxyethylene/aliphatic acid esters, aliphatic acid esters of polyglycerol, polyoxyethylated castor oil, diethanolamides of aliphatic acids, polyoxyethylene alkylamines, aliphatic acid partial esters of triethanolamine, trialkylamine oxides, and polyoxyalkylene-functional organopolysiloxanes. Use of a nonionic surfactant is preferred.

The content of the emulsifying agent is preferably from 0.1 to 20 weight parts, and particularly preferably from 0.5 to 10 weight parts, in each case, for each 100 weight parts of the crosslinked organic particles.

The water content is not critical but water preferably should constitute 5 to 99 weight % of the suspension, and more preferably 10 to 80 weight %.

Such suspensions may also contain other components including additives for stabilizing the dispersion or adjusting the viscosity such as ethanol or any water-soluble polymer such as xanthan gum, guar gum, carboxymethyl cellulose, polyvinyl alcohol, polyvinylpyrrolidone, carboxyvinyl polymers, hydroxyethyl cellulose, and polyoxyethylene glycol distearate; film-forming agents such as polymers of radically polymerizable (meth)acrylic monomers, copolymers of silicone compounds with radically polymerizable (meth)acrylic monomers, poly(N-acylalkylene imine)s, poly (N-methylpyrrolidone)s, and silicone resins that contain groups such as fluorinated organic groups, the amino, or silanol group; oxidation inhibitors such as BHA, BHT, and γ-orizanol; antifreezes such as ethanol, isopropyl alcohol, 1,3-butylene glycol, ethylene glycol, propylene glycol, and glycerol; antimicrobials and preservatives such as triclosan and triclocarban; pearlescent agents; chelating agents such as ethylene diamine tetraacetic acid, citric acid, ethane-1-hydroxy-1,1-diphosphonic acid, and their salts; UV absorbers including benzophenone derivatives such as 2-hydroxy-4-methoxybenzophenone, benzotriazole derivatives such as 2-(2'-hydroxy-5'-methylphenyl) benzotriazole, and cinnamic acid esters; colorants such as chromatogens, dyes, and pigments; spray-enabling agents; vitamins; hair tonics; growth promoters; hormones; fragrances; and perfumes.

These crosslinked organic particles and their suspensions are useful as components for imparting properties such as lubricity, softness, and flexibility to lubricants, cleaning agents, flatting agents, cosmetics, and materials employed in electrostatic development such as toners and carriers. They can also be used as components for imparting such properties as flatness, softness, and flexibility to paints and coatings; and as components for imparting such properties as lubricity and impact resistance to thermosetting resins and thermoplastic resins.

One method for preparing suspensions is by emulsifying a fluid composition containing components (A), (B), and (C) in water using emulsifying agent, and then crosslinking the composition by effecting hydrosilylation.

Another method for preparing suspensions is by emulsifying a fluid composition containing components (A) and (B) in water using emulsifying agent, thereafter adding component (C), and subsequently crosslinking the composition by effecting hydrosilylation.

Components (A), (B), and (C) used in these methods are the same components as described above. The emulsifying device used for the emulsifying agent-supported emulsification of the components (A)–(C) composition in water, for the emulsifying agent-supported emulsification of the components (A)+(B) composition in water, and for the addition of component (C) to the component (A)+(B) composition, can be exemplified by homomixers, paddle mixers, Henschel mixers, homodispersers, colloid mills, propeller-type stirrers, homogenizers, inline continuous emulsifiers, ultrasound emulsifiers, and vacuum mills.

Surfactants as described above can be used as the emulsifying agent in these methods, and the use of a nonionic surfactant is particularly preferred. The emulsifying agent is preferably added at from 0.1 to 20 weight parts, and particularly preferably at from 0.5 to 10 weight parts, in each case, for each 100 weight parts of the total of components (A) to (C). The amount of water is not critical, but water preferably should be present in an amount of from 5 to 99 weight % of the overall emulsion, and more preferably from 10 to 80 weight % of the overall emulsion.

The crosslinked organic particle suspension can be produced by heating the resulting emulsion of the fluid composition, or by holding this emulsion at room temperature to effect hydrosilylation-induced crosslinking of the water-dispersed fluid composition.

The resulting crosslinked organic particles have a spherical shape, and they should have an average particle size in the range from 0.1 to 500 μm, and preferably in the range from 0.1 to 200 μm. It is quite difficult to prepare crosslinked organic particles with an average particle size below the lower limit of the given range. Crosslinked organic particles with an average particle size exceeding the upper limit of the given range exhibit an increasingly impaired dispersibility when blended into organic resins, paints, coatings, and cosmetics.

The methods according to the invention include removing water from the crosslinked organic particle suspension. The technique to remove water is exemplified by spraying the suspension into a hot gas current, freeze-drying the suspension, and addition of salt to the suspension to aggregate the crosslinked organic particles, followed by thermal drying of the separated crosslinked organic particle slurry. The crosslinked organic particles are preferably used in a suspension form since the suspension form offers particularly good handling characteristics and blendability with other components.

EXAMPLES

Crosslinked organic particles, their suspensions, and methods for preparing such particles and suspensions are explained in greater detail below by reference to the following working examples. The viscosity values reported in these examples were measured at 25° C., while properties of the crosslinked organic particles were measured according to the procedures described below.

Durometer of the Crosslinked Organic Particles

The fluid composition used to produce the crosslinked organic particles was heated for 30 minutes in a forced circulation oven at 130° C. to produce a crosslinked organic sheet. The durometer of the sheet was measured using a type A durometer as described in Japanese Industrial Standard (JIS) K 6253-1997, and the resulting value was used as the durometer value for the crosslinked organic particles.

Average Particle Size of the Crosslinked Organic Particles

Measurement was carried out on a crosslinked organic particle suspension using a laser diffraction instrument for measuring particle size distributions, Model LA-500 from Horiba Seisakusho. A median diameter which is the particle diameter corresponding to 50% of the cumulative distribution, is reported as the average particle size of the crosslinked organic particles.

Affinities for Organic Oil and Silicone Oil Exhibited by the Crosslinked Organic Sheet and Crosslinked Organic Particles The fluid composition used to produce the crosslinked organic particles was heated for 30 minutes in a forced circulation oven at 130° C. to produce a crosslinked organic sheet. The sheet was cut into specimens with dimensions of 2 cm×2 cm×1 cm. Specimens were immersed for 24 hours in an organic oil or a silicone oil, after which the weight increase was determined. The weight of the contained oil expressed as a percentage calculated on the crosslinked organic sheet is reported as the oil absorption weight % of the crosslinked organic sheet.

For the crosslinked organic particles, a 5 gram sample was introduced into a 100-mL beaker. Then, while slowly stirring the crosslinked organic particles with a glass rod, the organic oil or the silicone oil was added one drop at a time, and the quantity of oil addition required to just produce a homogeneous paste of oil and the crosslinked organic particles was determined. The weight of the added oil expressed as a percentage of the crosslinked organic particles is reported as the oil absorption weight % of the crosslinked organic particles.

Example 1

A fluid composition was prepared by mixing the following to homogeneity at 5° C.: 100 weight parts of an allyl-terminated polypropylene oxide with a viscosity of 390 mPa·s and an average molecular weight of 3,000, 18 weight parts an organopolysiloxane with the formula

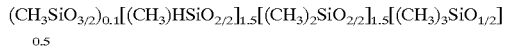

and a viscosity of 20 mPa·s, containing at least 3 silicon-bonded hydrogens in each molecule, and sufficient of an isopropanolic chloroplatinic acid solution to provide 50 weight-ppm of platinum metal in the composition.

An emulsion of this composition was subsequently prepared by rapidly mixing the composition into 100 weight parts of a 1.65 weight % aqueous polyoxyethylene (9 mol adduct) nonylphenyl ether solution adjusted to 25° C., emulsifying it with a colloid mill, and then introducing the product into 200 weight parts of pure water. A suspension of crosslinked organic particles was produced by carrying out hydrosilylation in the water-emulsified composition by holding the emulsion for 24 hours at 35° C. This suspension was dried by spraying into a hot gas current at 200° C. to provide spherical crosslinked organic particles composed of a rubbery material. The properties of these crosslinked organic particles are shown in Table 1.

Comparative Example 1

A fluid composition was prepared by mixing the following to homogeneity: 100 weight parts of an allyl-terminated polypropylene oxide with a viscosity of 390 mpa·s and an average molecular weight of 3,000), 1 weight part of divinylbenzene, and 1 weight part of azobisisobutyronitrile. A homogeneous emulsion of this composition was subsequently prepared by rapidly mixing the composition into 100 weight parts of a 2.5 weight % aqueous polyoxyethylene (9 mol adduct) nonylphenyl ether solution adjusted to 25° C., and passing the resulting mixture through a colloid mill. Radical polymerization was carried out on this emulsion by heating it for 4 hours at 80° C. with stirring. A slight evolution of heat was observed. Drying the resulting emulsion in a 100° C. oven in an aluminum dish produced a white turbid liquid, but organic resin particles were not obtained.

Example 2

A fluid composition was prepared by mixing 12.3 weight parts of 1,5-hexadiene with a molecular weight of 82.15, and 87.7 weight parts of a trimethylsiloxy-endblocked dimethylsiloxane-methylhydrogensiloxane copolymer with a viscosity of 50 mPa·s containing at least 3 silicon-bonded hydrogens in each molecule. An emulsion of this composition was subsequently prepared by rapidly mixing the composition into 100 weight parts of a 1.65 weight % aqueous polyoxyethylene (9 mol adduct) nonylphenyl ether solution, emulsifying it with a colloid mill, and then introducing the product into 200 weight parts of pure water.

Into this emulsion was then admixed a separately prepared water-based emulsion of a platinum catalyst. The platinum catalyst contained 1,1-divinyl-1,1,3,3-tetramethyldisiloxane as solvent and a Pt/1,1-divinyl-1,1,3,3-tetramethyldisiloxane complex as the catalytic component. The average particle size of the platinum catalyst in the catalyst emulsion was 0.05 μm, and the platinum metal concentration in the catalyst emulsion was 0.05 weight %. The catalyst emulsion was added in a sufficient quantity to provide 20 weight-ppm of platinum metal based on the total weight of 1,5-hexadiene and the dimethylsiloxane-methylhydrogensiloxane copolymer in the first described emulsion. A suspension of crosslinked organic particles was then produced by carrying out hydrosilylation-mediated crosslinking in the water-emulsified composition by holding the overall emulsion for 24 hours at 35° C. Removal of water by spraying the suspension into a hot gas current at 200° C. yielded spherical crosslinked organic particles composed of a rubbery material. The properties of these crosslinked organic particles are shown in Table 1.

Comparative Example 2

A fluid composition was prepared by mixing 94.0 weight parts of a dimethylvinylsiloxy-endblocked dimethylpolysiloxane with a viscosity of 400 mPa·s, and 6.0 weight parts of a trimethylsiloxy-endblocked dimethylsiloxane-methylhydrogensiloxane copolymer with a viscosity of 50 mPa·s containing at least 3 silicon-bonded hydrogens in each molecule. An emulsion of this composition was subsequently prepared by rapidly mixing the composition into 100 weight parts of a 1.65 weight % aqueous polyoxyethylene (9 mol adduct) nonylphenyl ether solution, emulsifying it with a colloid mill, and then introducing the product into 200 weight parts of pure water.

Into this emulsion was then admixed a separately prepared water-based emulsion of a platinum catalyst. The platinum catalyst contained 1,1-divinyl-1,1,3,3-tetramethyldisiloxane as solvent and a Pt/1,1-divinyl-1,1,3,3-tetramethyldisiloxane complex as the catalytic component. The average particle size of the platinum catalyst in the catalyst emulsion was 0.05 μm, and the platinum metal concentration in the catalyst emulsion was 0.05 weight %. The catalyst emulsion was added in a sufficient quantity to provide 20 weight-ppm of platinum metal based on the total amount of the dimethylvinylsiloxy-endblocked dimethylpolysiloxane in the first-described emulsion. A suspension of silicone rubber particles was then produced by carrying out an hydrosilylation-mediated crosslinking in the water-emulsified composition by holding the overall emulsion for 24 hours at 35° C. This suspension was dried by spraying into a hot gas current at 200° C. to provide spherical silicone rubber particles. The properties of these silicone rubber particles are shown in Table 1.

Comparative Example 3

50 weight parts of an acrylonitrile-butadiene copolymer rubber in the form of product number N240S of Japan Synthetic Rubber, and 3 weight parts of 1,3,5,7-tetramethylcyclotetrasiloxane were mixed at 150° C. in a kneader. The mixture was cooled to 100° C., at which point 0.5 weight part of chloroplatinic acid hexahydrate was added with mixing to homogeneity. This was followed by kneading for 5 minutes on a heated two-roll mill at 150° C. The resulting mixture lacked any fluidity and was resistant to emulsification. The mixture was press-cured at 200° C. under pressure to provide a crosslinked organic rubber sheet. While cooling with dry ice, the sheet was crushed using a hammer mill and yielded irregularly shaped crosslinked organic particles having an average particle size of about 1 mm.

TABLE 1

|  | Example 1 | Example 2 | Comp. Ex. 2 | Comp. Ex. 3 |
|---|---|---|---|---|
| durometer | 45 | 60 | 31 | 68 |
| average particle size, μm | 4 | 4 | 4 | 1000 |
| oil absorption (wt %) of the crosslinked sheet | | | | |
| organic oil | 43 | 28 | 16 | 59 |
| silicone oil | 15 | 9 | 230 | 72 |
| oil absorption (wt %) of the crosslinked particles | | | | |
| organic oil | 190 | 62 | 50 | 60 |
| silicone oil | 30 | 20 | 360 | 70 |

Application as a Cosmetic Component

Three liquid cosmetics were produced by stirring the following components for 5 minutes at 2,500 rpm with a homodisperser: 74 weight parts of the suspension prepared in Example 1, Example 2, or Comparative Example 2; 5 weight parts of octyl p-methoxycinnamate; 1 weight part of α-monoisostearyl glyceryl ether polyoxyethylene sorbitan monooleate; 2 weight parts of beeswax; 2 weight parts of lanolin; 10 weight parts of squalane; 5 weight parts of liquid paraffin; a preservative in an appropriate amount; and a fragrance in an appropriate amount. A fourth liquid cosmetic was produced by stirring the following components for 5 minutes at 2,500 rpm with a homodisperser: 29 weight parts of the crosslinked organic particles produced in Comparative Example 3; 5 weight parts of octyl p-methoxycinnamate; 1 weight part of α-monoisostearyl glyceryl ether polyoxyethylene sorbitan monooleate; 2 weight parts of beeswax; 2 weight parts of lanolin; 10 weight parts of squalane; 5 weight parts of liquid paraffin; 45 weight parts of purified water; a preservative in an appropriate amount; and a fragrance in an appropriate amount. The resulting cosmetics were evaluated as described below, and the results of these evaluations are shown in Table 2.

Spread Ability on the Skin

The cosmetic was used by the members of a 10-person panel. A report of a good sensation in this category by 8 to 10 panelists was scored as +. A report of a good sensation by 4 to 7 panelists was scored as Δ. A report of a good sensation by 0–3 panelists was scored as x.

Skin Smoothness

The cosmetic was used by the members of a 10-person panel. A report of a good sensation in this category by 8 to 10 panelists was scored as +. A report of a good sensation by 4 to 7 panelists was scored as Δ. A report of a good sensation by 0–3 panelists was scored as x.

TABLE 2

| source of the crosslinked particles | Example 1 | Example 2 | Comp. Ex. 2 | Comp Ex. 3 |
|---|---|---|---|---|
| spread ability on the skin | + | + | Δ stiff | x poor |
| skin smoothness | + | + | x stiff | x strong foreign substance sensation |

The crosslinked organic particles according to the invention have a spherical shape and a good dispersibility in thermoplastic resins, thermosetting resins, paints, coatings, cosmetics, rubbers, and toners and carriers employed in electrostatic development. The methods for preparing these crosslinked organic particles are an highly efficient production of the crosslinked organic particles. These crosslinked organic particles and their suspensions have excellent handling characteristics and excellent blendability with other components. The methods for preparing the crosslinked organic particle suspensions are an highly efficient production of suspensions.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of preparing a suspension of spherical crosslinked organic particles whose average particle size is from 0.1–500 μm by emulsifying in water using an emulsifying agent, a fluid composition comprising (A) an organic compound that has at least 2 aliphatically unsaturated bonds in each molecule selected from the group consisting of a diene, a diene oligomer, and a polyether, (B) a silicon-containing organic compound that has at least 2 silicon-bonded hydrogen atoms in each molecule, (C) an hydrosilylation reaction catalyst, and crosslinking the fluid composition by carrying out an hydrosilylation reaction.

2. A method according to claim 1 wherein component (B) is an organohydrogenpolysiloxane.

3. A method of preparing spherical crosslinked organic particles having an average particle size of 0.1–500 μm by emulsifying in water using an emulsifying agent, a fluid composition comprising (A) an organic compound that has at least 2 aliphatically unsaturated bonds in each molecule selected from the group consisting of a diene, a diene oligomer, and a polyether, (B) a silicon-containing organic compound that has at least 2 silicon-bonded hydrogen atoms in each molecule, and (C) an hydrosilylation reaction catalyst, crosslinking the fluid composition by carrying out an hydrosilylation reaction, and thereafter removing water.

4. A method according to claim 3 wherein component (B) is an organohydrogenpolysiloxane.

* * * * *